United States Patent [19]
DeGeorge et al.

[11] Patent Number: 6,147,126
[45] Date of Patent: *Nov. 14, 2000

[54] GAS CONVERSION USING HYDROGEN FROM SYNGAS GAS AND HYDROCONVERSION TAIL GAS

[75] Inventors: Charles W. DeGeorge, Chester, N.J.; Robert J. Wittenbrink, Baton Rouge, La.; Thomas M. Stark, Morristown, N.J.

[73] Assignee: Exxon Research and Engineering Company, Florham Park, N.J.

[ * ] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 09/021,476

[22] Filed: Feb. 10, 1998

[51] Int. Cl.$^7$ .................................................. C07C 27/00
[52] U.S. Cl. ..................... 518/715; 518/700; 518/702; 518/703; 518/709; 518/715; 518/722; 252/373; 208/56; 208/59
[58] Field of Search .................................. 518/702, 703, 518/709, 715, 722, 700; 252/373; 208/56, 59

[56] References Cited

U.S. PATENT DOCUMENTS

| | | |
|---|---|---|
| 3,890,113 | 6/1975 | Child et al. .......................... 48/197 R |
| 4,049,741 | 9/1977 | Kuo et al. ............................. 260/676 R |
| 5,260,239 | 11/1993 | Hsia ........................................... 502/30 |
| 5,322,617 | 6/1994 | De Bruijn et al. ...................... 208/108 |
| 5,844,005 | 12/1998 | Bauman et al. ........................ 518/700 |

FOREIGN PATENT DOCUMENTS

| | | | |
|---|---|---|---|
| 0109702 | 5/1984 | European Pat. Off. | .......... C07C 1/04 |
| 0269297 | 6/1988 | European Pat. Off. | ........ C07C 15/00 |
| 0512635 | 11/1992 | European Pat. Off. | .......... C07C 1/08 |

OTHER PUBLICATIONS

D. M. Bibby, et al (eds), Syngas for $C_1$–Chemistry. Limits of the Steam Reforming Process, Methane Conversion, pp. 73–78, (Elsevier, 1988).

*Primary Examiner*—Johann Richter
*Assistant Examiner*—J. Parsa
*Attorney, Agent, or Firm*—Jay Simon; Jonathan N. Provoost

[57] ABSTRACT

A gas conversion process including catalytic hydrocarbon synthesis from a synthesis gas comprising a mixture of $H_2$ and CO, produces hydrogen from the synthesis gas and upgrades synthesized hydrocarbons by one or more hydroconversion operations which utilize this hydrogen. The hydroconversion also produces a hydrogen rich tail gas which is used in the process for at least one of (i) hydrocarbon synthesis catalyst rejuvenation, (ii) the hydrocarbon synthesis, and (iii) hydrogen production. In one embodiment the tail gas is used to hydrodesulfurize sulfur-containing hydrocarbon liquids recovered from the natural gas used to form the synthesis gas. The hydrogen production is accomplished by physical separation, such as PSA, with or without chemical means such as a water gas shift reaction.

13 Claims, 2 Drawing Sheets

GAS CONVERSION USING HYDROGEN FROM SYNGAS GAS AND HYDROCONVERSION TAIL GAS

BACKGROUND OF THE DISCLOSURE

1. Field of the Invention

The invention relates to a gas conversion process including synthesizing and hydroconverting hydrocarbons, wherein synthesis gas hydrogen and hydroconversion tail gas hydrogen are used in the process. More particularly, the invention relates to a gas conversion process comprising synthesizing hydrocarbons from a synthesis gas and hydroconverting the synthesized hydrocarbons with hydrogen produced from the synthesis gas, wherein the hydroconversion produces a tail gas rich in hydrogen which is used for one or more of the hydrocarbon synthesis, rejuvenation of the synthesis catalyst, hydrogen production, and hydrodesulfurizing well gas condensate.

2. Background of the Invention

Hydrocarbon synthesis processes are known in which a synthesis gas feed comprising a mixture of $H_2$ and CO is fed into a hydrocarbon synthesis reactor in which it reacts in the presence of a Fischer-Tropsch catalyst under conditions effective to form higher molecular weight hydrocarbons. These processes include fixed bed, fluid bed and slurry hydrocarbon synthesis, all of which are well documented in various technical articles and in patents. In many cases it is desired that the synthesized hydrocarbons comprise mostly $C_{5+}$ hydrocarbons (e.g., $C_{5+}-C_{200}$) and preferably $C_{10+}$ hydrocarbons, at least a portion of which are solid at standard conditions of room temperature and pressure. It is preferred in a slurry hydrocarbon synthesis process that the hydrocarbons comprise mostly $C_{5+}$ paraffins. These hydrocarbons are upgraded to more valuable products by one or more hydroconversion operations in which at least a portion of the molecular structure is changed by reacting with hydrogen. Hydroconversion operations therefore all require hydrogen. Hydrogen is also required for rejuvenating the hydrocarbon synthesis catalyst and sometimes for maintaining or changing the $H_2$ to CO ratio of the syngas feed for the hydrocarbon synthesis. Further, the production of natural gas from a gas well also produces valuable, sulfur-containing hydrocarbon liquids which need to be hydrodesulfurized to form products. It is desirable to have a hydrocarbon synthesis process in which hydrogen required for the hydrocarbon synthesis catalyst rejuvenation, hydroconversion upgrading of the synthesized hydrocarbons and also hydrodesulfurizing of the well liquids is obtained from within the overall, integrated process or plant itself, rather than depending on an outside source of hydrogen.

SUMMARY OF THE INVENTION

The invention relates to a process for producing both hydrocarbons and hydrogen from a synthesis gas (syngas) comprising a mixture of $H_2$ and CO, and upgrading at least a portion of the hydrocarbons by one or more hydroconversion operations, with the hydrogen used for the hydroconversion produced from the syngas and wherein hydrogen rich, hydroconversion reactor tail gas is used in the gas conversion process. Gas conversion process in the context of the invention is meant to include at least hydrocarbon synthesis, hydrogen production from syngas, and hydroconversion of at least a portion of the synthesized hydrocarbons. By hydroconversion is meant a process in which the molecular structure of the hydrocarbon is changed by reacting it with hydrogen. The hydroconversion reactor tail gas is used for at least one of hydrocarbon synthesis (HCS), for HCS catalyst rejuvenation, to adjust the $H_2$ to CO mole ratio in the HCS reactor, and to increase the purity of the hydrogen produced from the syngas. In an embodiment in which the syngas is produced from a natural gas from which sulfur-containing hydrocarbon liquids are recovered as condensate, the tail gas is used to provide the hydrogen for removing the sulfur compounds from the liquids and the gas conversion process includes forming the syngas (also referred to as syngas generation). The sulfur is removed from the hydrocarbon liquids by reacting it with hydrogen in the presence of a suitable catalyst at conditions effective for removing the sulfur (hereinafter "hydrodesulfurizing"). In a broad sense the invention comprises synthesizing hydrocarbons, and producing hydrogen from a syngas, using the hydrogen for hydroconverting at least a portion of the synbthesized hydrocarbons and producing a hydrogen rich hydroconversion reactor tail gas, and using the tail gas for one or more operations associated with the hydrocarbon synthesis and syngas hydrogen production. More specifically, the invention comprises a gas conversion process including hydrocarbon synthesis, hydroconversion and hydrogen production from synthesis gas comprising a mixture of $H_2$ and CO, which comprises contacting said synthesis gas with a hydrocarbon synthesis catalyst, reacting said $H_2$ and CO in the presence of said synthesis catalyst at reaction conditions effective to form hydrocarbons, and reacting at least a portion of said hydrocarbons with hydrogen in the presence of a hydroconversion catalyst to alter the molecular structure of at least a portion of said hydrocarbons and produce a hydrogen rich tail gas, wherein said tail gas is used for at least one of (i) said synthesis, (ii) said hydrogen production, and (iii) rejuvenation of said hydrocarbon synthesis catalyst, and wherein said hydrogen used for said hydroconversion is produced from said synthesis gas. A further embodiment uses the tail gas for hydrodesulfurizing sulfur-containing hydrocarbon liquids recovered from natural gas. The hydrogen is produced from the syngas using one or more of (a) physical separation means such as pressure swing adsorption (PSA), membrane separation or thermal swing adsorption (TSA), and (b) chemical means such as a water gas shift reaction. Physical means for the hydrogen production will typically be used to separate the hydrogen from the syngas, irrespective of whether or not chemical means such as a water gas shift reaction is used, in order to obtain hydrogen of the desired degree of purity (e.g., at least about 80%).

The hydrocarbon gas component of the syngas feed, while conveniently derived from natural gas which comprises mostly methane, may be obtained by any available and convenient means from any suitable hydrocarbonaceous material, including coal and hydrocarbon liquids. The process used to form the syngas may also be any process that is convenient, but will more typically and preferably be a process which partially oxidizes and/or steam reforms the hydrocarbon gas, with or without the presence of a catalyst. The hydrocarbon synthesis is accomplished by reacting the syngas in an HCS reaction zone or reactor, in the presence of a Fischer-Tropsch catalyst, at conditions effective to form hydrocarbons and preferably $C_{5+}$ hydrocarbons. As is known, during the HCS reaction the HCS catalyst reversibly deactivates due to the presence of catalyst deactivating species, such as nitrogen compounds present in the syngas (e.g., HCN and $NH_3$) and possibly others formed by the HCS reaction. It is also known that the catalytic activity is restored (rejuvenated) by contacting the catalyst with hydrogen or a gas comprising hydrogen. At least a portion of the synthesized hydrocarbon product removed from the HCS reactor is upgraded by at least one hydroconversion operation, to reduce its viscosity or pour point, or to convert the synthesized hydrocarbons into boiling point fractions of higher value. Such hydroconversion operations also require hydrogen. In an integrated HCS plant or unit, it is preferred if at all possible that the integrated plant produce its own hydrogen, or at least a portion of the hydrogen needed for one or more of these uses within the plant, rather than be dependent on an outside source.

Producing hydrogen from the syngas using physical separation means provides relatively pure hydrogen, along with an offgas which comprises a hydrogen depleted and CO rich mixture of $H_2$ and CO. This offgas may be used as fuel or fed into the HCS reaction zone. If the demand for hydrogen is greater than can be met by separating hydrogen from the syngas, or if an ancillary or alternate means for producing hydrogen is desired, chemical means such as a water gas shift reactor may be used to produce, from the syngas, all or a portion of the hydrogen required. In this embodiment, at least one of (a) a portion of the syngas and (b) the CO rich offgas resulting from physically separating hydrogen from the syngas, are fed into a water gas shift reactor in the presence of steam and a water gas shift catalyst to form a mixture of $H_2$ and $CO_2$ from the CO and steam, which is then passed through physical separation means to separate the $H_2$ from the rest of the gas and form relatively pure $H_2$, and a CO rich offgas, with the offgas recycled back into either the HCS reaction zone, into the shift reactor, or used as fuel.

DETAILED DESCRIPTION

Figure 1:
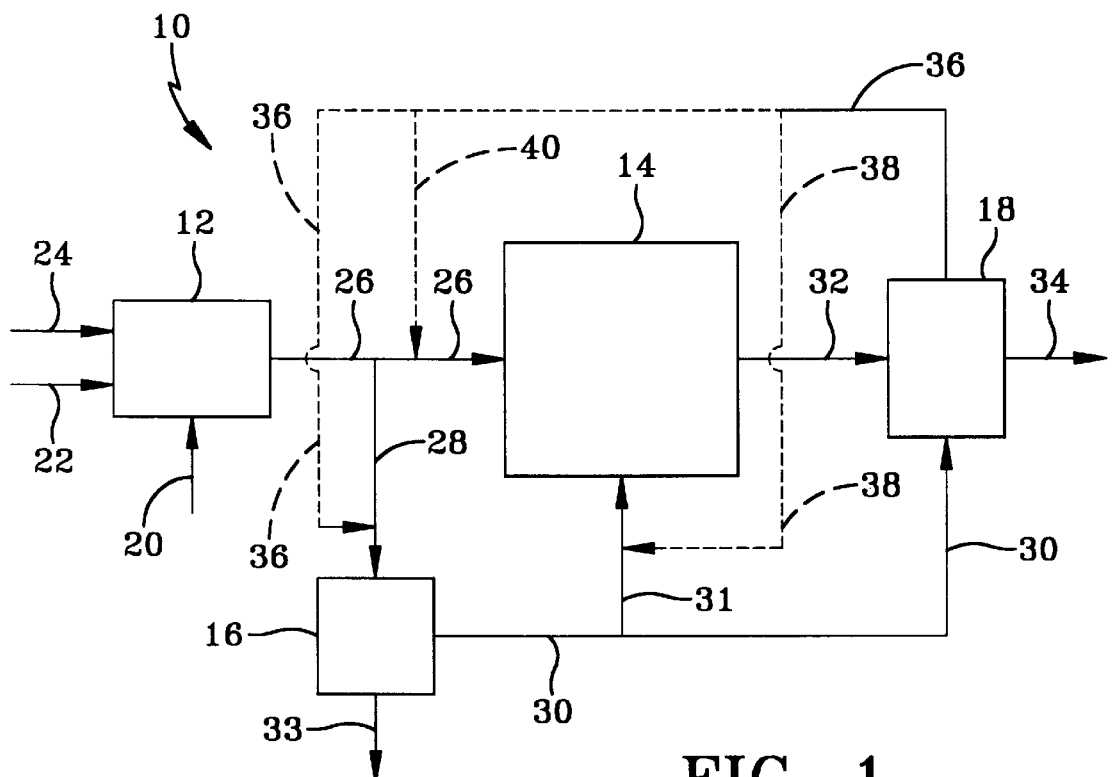
FIG. 1 is a block flow diagram of the process of the invention starting with syngas production and showing recycle of the tail gas.

At least a portion of the hydrocarbons produced by an HCS process according to the invention are upgraded to more valuable products, by subjecting all or a portion of the $C_{5+}$ hydrocarbons to hydroconversion. By hydroconversion is meant one or more operations in which the molecular structure of at least a portion of the hydrocarbon is changed by reacting it with hydrogen in the presence of a catalyst and includes, for example, hydroisomerization, hydrocracking, hydrodewaxing, hydrorefining, and the more severe hydrorefining referred to as hydrotreating, all conducted at conditions well known in the literature for hydroconversion of hydrocarbon feeds, including hydrocarbon feeds rich in paraffins. Illustrative, but nonlimiting examples of more valuable products formed by conversion include one or more of a synthetic crude oil, liquid fuel, olefins, solvents, lubricating, industrial or medicinal oil, waxy hydrocarbons, nitrogen and oxygen containing compounds, and the like. Liquid fuel includes one or more of motor gasoline, diesel fuel, jet fuel, and kerosene, while lubricating oil includes, for example, automotive, jet, turbine and metal working oils. Industrial oil includes well drilling fluids, agricultural oils, heat transfer fluids and the like. Illustrative, but nonlimiting examples of hydroconversion processes useful in the practice of the invention are disclosed in U.S. Pat. Nos. 4,832,819; 4,943,672; 5,059,299; 5,378,348 and 5,457,253.

The hydrocarbon component of the feed for the syngas generation, while conveniently derived from natural gas which comprises mostly methane as the hydrocarbon component, may be obtained by any available and convenient means from any suitable hydrocarbonaceous material, including coal, coke, hydrocarbon liquids and gas, as is well known. Typically a gas conversion plant will be proximate a source of such hydrocarbonaceous materials and the syngas generating operation will be an integral part of the plant. Feeds comprising a low molecular weight (e.g., $C_1$–$C_4$) hydrocarbon, preferably alkane and more preferably mostly methane, as in natural gas, are preferred. Natural gas is particularly preferred because it comprises primarily methane, is convenient, clean and doesn't leave large quantities of ash, shale, sulfur compounds and the like to be handled and disposed of. The syngas may be formed by various means, including contacting a hot carbonaceous material, such as coal, coke or tar, with steam and from burning such material under partial oxidation conditions to form methane or a low molecular weight hydrocarbon gas which is then fed into a syngas generator. In syngas generation, a low molecular weight hydrocarbon, typically a $C_1$–$C_4$ alkane, and preferably methane as in natural gas, along with steam, oxygen or air is fed into a syngas generating unit. In a syngas generator, the hydrocarbon gas is partially oxidized with oxygen or air, steam reformed, or partially oxidized and either steam reformed or passed into a water gas shift reactor. Steam reforming is accomplished with the steam reforming catalyst in either a fixed or fluid bed, with a fluid bed having superior mixing and heat transfer characteristics. In catalytic partial oxidation, the hydrocarbon component of the feed to the syngas generator is premixed with oxygen, and optionally steam, and passed into the syngas generator in which it reacts in the presence of a noble metal catalyst and preferably a supported noble metal catalyst as is known. In a fluid bed syngas generating (FBSG) process, the partial oxidation and steam reforming both occur in the presence of the steam reforming catalyst. FBSG is disclosed, for example, in U.S. Pat. Nos. 4,888,131 and 5,160,456. In autothermal reforming, partial oxidation occurs in the absence of a catalyst and precedes adiabatic steam reforming which occurs in a fixed bed of catalyst. The syngas exiting the reactor comprises a mixture of $H_2$ and CO along with water vapor or steam, nitrogen, $CO_2$ and minor amounts of unreacted methane. The amount of $CO_2$ present in the feed to the syngas generator will effect the reaction equilibrium and may be used, along with the conditions in the unit, to adjust the $H_2$ to CO ratio of the syngas. Most of the water is removed from the syngas before it is passed into an HCS reactor. Irrespective of either the source of the hydrocarbon for the syngas production or the process, such hydrocarbon feeds invariably contain elemental nitrogen or nitrogen containing compounds which react in the syngas generator to form nitrogenous species, such as HCN and $NH_3$, which reversibly deactivate the HCS catalyst during the HCS reaction.

In an HCS process, liquid and gaseous hydrocarbon products are formed by contacting a syngas comprising a mixture of $H_2$ and CO with a Fischer-Tropsch type of HCS catalyst, under shifting or non-shifting conditions and preferably under non-shifting conditions in which little or no water gas shift reaction occurs, particularly when the catalytic metal comprises Co, Ru or mixture thereof. Suitable Fischer-Tropsch reaction types of catalyst comprise, for example, one or more Group VIII catalytic metals such as Fe, Ni, Co, Ru and Re. In one embodiment the catalyst comprises catalytically effective amounts of Co and one or more of Re, Ru, Fe, Ni, Th, Zr, Hf, U, Mg and La on a suitable inorganic support material, preferably one which comprises one or more refractory metal oxides. Preferred supports for Co containing catalysts comprise titania, particularly when employing a slurry HCS process in which higher molecular weight, primarily paraffinic liquid hydrocarbon products are desired. Useful catalysts and their preparation are known and illustrative, but nonlimiting examples may be found, for example, in U.S. Pat. Nos. 4,568,663; 4,663,305; 4,542,122; 4,621,072 and 5,545,674.

With respect to the hydrocarbon synthesis, fixed bed, fluid bed and slurry hydrocarbon synthesis (HCS) processes for forming hydrocarbons from a syngas comprising a mixture of $H_2$ and CO are well known and documented in the literature. In all of these processes the syngas is reacted in the presence of a suitable Fischer-Tropsch type of hydrocarbon synthesis catalyst, at reaction conditions effective to form hydrocarbons. Some of these hydrocarbons will be liquid, some solid (e.g., wax) and some gas at standard room temperature conditions of temperature and pressure of 25° C. and one atmosphere, particularly if a catalyst having a catalytic cobalt component is used. Slurry HCS processes are often preferred because of their superior heat (and mass) transfer characteristics for the strongly exothermic synthesis reaction and because they are able to produce relatively high molecular weight, paraffinic hydrocarbons when using a cobalt catalyst. In a slurry HCS process a syngas comprising a mixture of $H_2$ and CO is bubbled up as a third phase through a slurry in a reactor which comprises a particulate Fischer-Tropsch type hydrocarbon synthesis catalyst dispersed and suspended in a slurry liquid comprising hydrocarbon products of the synthesis reaction which are liquid at the reaction conditions. The mole ratio of the hydrogen to the carbon monoxide may broadly range from about 0.5 to 4, but is more typically within the range of from about 0.7 to 2.75 and preferably from about 0.7 to 2.5. The stoichiometric mole ratio for a Fischer-Tropsch HCS reaction is 2.0, but in the practice of the present invention it may be increased to obtain the amount of hydrogen desired from the syngas for other than the HCS reaction. In a slurry HCS process the mole ratio of the $H_2$ to CO is typically about 2.1/1. Slurry HCS process conditions vary somewhat depending on the catalyst and desired products. Typical conditions effective to form hydrocarbons comprising mostly $C_{5+}$ paraffins, (e.g., $C_{5+}$–$C_{200}$) and preferably $C_{10+}$ paraffins, in a slurry HCS process employing a catalyst comprising a supported cobalt component include, for example, temperatures, pressures and hourly gas space velocities in the range of from about 320–600° F., 80–600 psi and 100–40,000 V/hr/V, expressed as standard volumes of the gaseous CO and $H_2$ mixture (0° C., 1 atm) per hour per volume of catalyst, respectively. During the hydrocarbon synthesis operation, the HCS catalyst loses activity (deactivates) by deactivating species mentioned above present in the syngas and resulting from the synthesis reaction. This deactivation is reversible and catalytic activity is restored (the catalyst rejuvenated) by contacting the deactivated catalyst with hydrogen. The activity of the HCS catalyst in the reactive slurry is intermittently or continuously rejuvenated by contacting the slurry with hydrogen or a hydrogen containing gas to form a catalyst rejuvenated slurry either in-situ in the HCS reactor or in an external rejuvenation vessel, as is disclosed, for example, in U.S. Pat. Nos. 5,260,239; 5,268,344, and 5,283,216.

Physical separation processes useful for producing hydrogen from the syngas include adsorption-desorption processes and membrane separation, both of which are well known and commercially available. Adsorption-desorption processes include TSA and PSA, both of which comprise a plurality of adsorbent containing vessels operated in a cyclic manner. Adsorbents include molecular sieves, silica gel and activated carbon. The difference between pressure swing adsorption and thermal swing adsorption, is that the gas constituents other than hydrogen which are primarily adsorbed by the adsorbent during the adsorption part of the cycle are desorbed from the adsorbent during regeneration by a pressure swing cycle in PSA, as opposed to a thermal swing cycle in thermal swing adsorption. The pressure differential between adsorption and desorption is typically on the order of at least a magnitude. During operation, the feed gas, which in this case is a slip stream of the syngas, is fed into one or more vessels or adsorption zones in which the syngas components other than hydrogen (along with a minor amount of hydrogen) are adsorbed by the adsorbent. When the adsorbent has achieved capacity, the feed flow into the vessel is shut off, the pressure reduced and the adsorbed non-hydrogen components of the syngas are desorbed and removed as a purge gas. If desired, some hydrogen can be used to sweep the vessel at the end of the desorption cycle. The vessel is repressurized and placed back on stream for the next adsorption cycle. Thus, the purge gas contains the CO and any other non-hydrogen syngas components, along with a minor amount of hydrogen. This purge gas is the adsorption offgas which may be sent to disposal or burned as fuel, but which is preferably recycled back into one or more HCS reactors as part of the feed to utilize the valuable CO for the hydrocarbon synthesis. The hydrogen separated from the syngas during the adsorption is typically 99% pure and even purer than 99%. A typical PSA unit has at least one vessel on adsorption, while at least one other vessel is being depressurized and purged, with yet at least one other vessel being repressurized. In membrane separation, bundles of hollow fibers are present in the vessel and the syngas is passed into the vessel in which it flows over the outside of the fibers and out of the vessel. A hydrogen rich permeate gas forms inside each fiber and is removed as a separate, permeate stream. In a typical installation a plurality of such vessels are connected in series, with the permeate from each vessel being the feed into the next successive vessel. High capacity is achieved by using parallel sets of series units. The hydrogen is typically not as pure as that achieved with PSA, but is generally at least about 80% pure. The non-permeate effluents are combined as a CO rich offgas which is utilized in the same manner as for that recovered from the PSA separation. Yet another embodiment of physical separation comprises a combination of PSA or TSA adsorption-desorption and membrane separation. In a typical separation process of this type, the syngas is first passed through a membrane unit to produce a hydrogen-rich gas stream as the permeate. This hydrogen-rich permeate is then passed through a PSA or TSA unit to produce the high purity hydrogen stream and a CO-rich offgas stream. With this process, the amount of offgas produced is less than that obtained using either method by itself.

When using a water gas shift reaction to produce hydrogen, a portion or slip stream of syngas is passed into a water gas shift reactor in which the CO reacts with water vapor in the presence of a shift catalyst, such as nickel on a refractory metal oxide support, at reaction conditions effective to form a mixture of $H_2$ and $CO_2$ which exits the shift reactor, along with the other syngas components, including unreacted CO. If desired, the $CO_2$ may be removed from the shift reactor effluent by means well known to those skilled in the art, such as amine scrubbing. A commercially available process which employs hindered amine scrubbing for $CO_2$ removal is Exxon's Flexsorb® process. The hydrogen rich shift reactor effluent, with or without $CO_2$ removal and, after cooling and drum separation (not shown) for removal of any excess water, is passed through physical separation means for separating the hydrogen from the CO and other non-hydrogen components present in the gas, to form a relatively pure stream of hydrogen and a CO containing offgas. These gas streams are then utilized in the same manner as above, but with the CO containing offgas typically burned as fuel due to the lower CO content of the offgas. Whether or not a shift reactor is employed depends on the amount of hydrogen desired and the capacity of the syngas generator to satisfy the syngas requirements for both the hydrocarbon synthesis and the hydrogen production.

Figure 2:
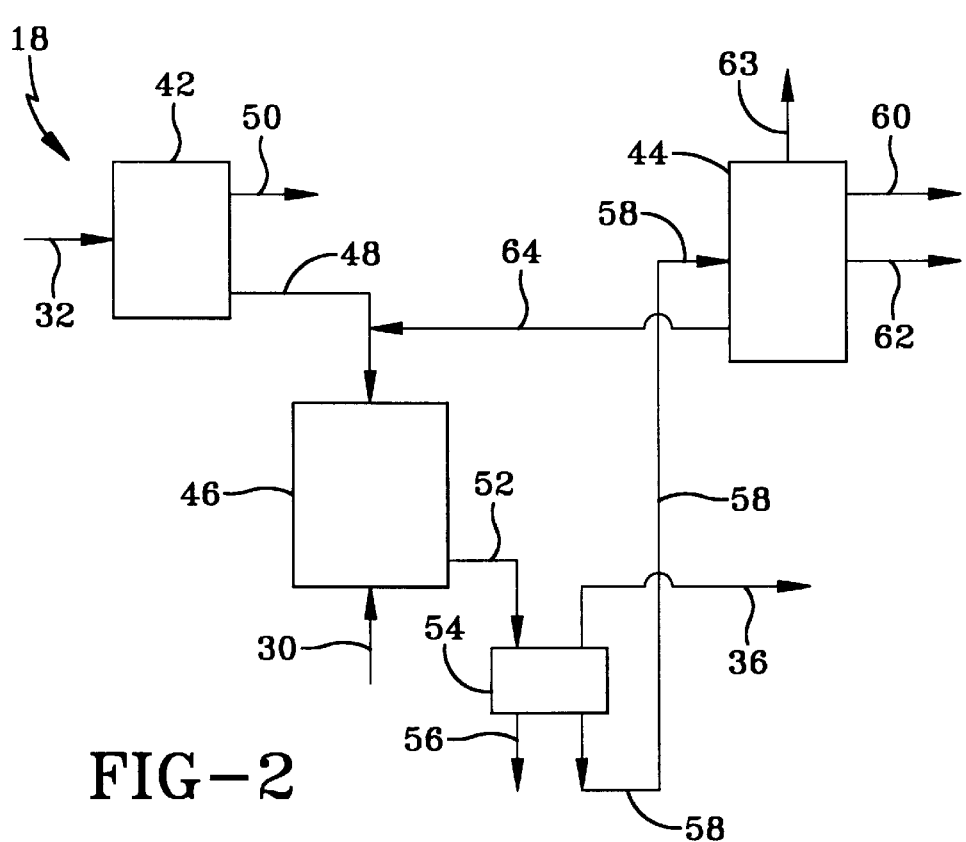
FIG. 2 illustrates details of the hydroconversion and hydrogen rich tail gas recovery.

Referring to FIG. 1, an integrated gas conversion plant 10 comprises an FBSG syngas generating unit 12, a slurry HCS reactor 14, a means 16 for producing hydrogen from syngas, and with box 18 comprising a hydroconversion unit. Natural gas, oxygen and steam are fed into the FBSG unit via lines 20, 22 and 24, respectively to generate syngas comprising a mixture of $H_2$ and CO. Based on 100 moles per hour of CO entering the slurry HCS reactor 14, the syngas stream passed from the syngas generator 12 into line 26 comprises 218 moles per hour of hydrogen and 104 moles per hour of CO, with an $H_2$ to CO mole ratio of about 2.1:1. A commercial scale plant will be much larger, processing as much as 100,000 or more moles per hour of CO. Hereinafter, all numbers will refer to moles per hour unless otherwise indicated. Of this, 209 moles of hydrogen and 100 of CO are passed into the HCS reactor 14 via line 26. The HCS reactor contains a catalyst comprising a supported catalytic cobalt component and is designed to operate at 80% conversion of the CO. A syngas slip stream containing 9 moles of hydrogen and 4 of CO is withdrawn from line 26, via line 28, and passed into the hydrogen producing unit 16. In the embodiment in which a PSA unit is used, typically a stream of at least 99% hydrogen is produced, with the remainder being low molecular weight hydrocarbons and nitrogen. For the purposes of this example, 85% of the hydrogen is separated from the slip stream using molecular sieves for the adsorption separation. Eight moles of hydrogen are passed into line 30, with the $H_2$ depleted and CO rich offgas produced by the hydrogen separation withdrawn via line 33 comprising 1 mole of hydrogen and 4 moles of CO. In this embodiment, the offgas is then used as a low BTU value fuel gas. Of the eight moles of hydrogen leaving the PSA unit, 5 moles are sent into the hydroconversion unit via line 30 to provide the hydrogen for the hydroisomerization of the synthesized hydrocarbons, with 3 moles passed to the HCS catalyst rejuvenation means (not shown) via line 31 for catalyst rejuvenation as is discussed below. The hydrocarbons produced in the HCS reactor are removed via line 32 and passed into the hydroconversion unit 18 in which they are fed, along with hydrogen from line 30, into a hydroisomerization reactor (shown as 46 in FIG. 2) to produce lower boiling material and in which the heavy, 700° F.+ hydrocarbons are converted into 700° F.− hydrocarbons. The hydrocarbons are hydroisomerized by reacting with $H_2$ in the presence of a suitable hydroisomerization catalyst, such as a cobalt-molybdenum catalyst on a silica-alumina support, at a 700° F.+ fraction conversion of 50 wt. %. This means that with each pass through the reactor, 50 wt. % of the 700° F.+ material is converted into 700° F.− material having a boiling point of less than 700° F. The hydroisomerized, 700° F.− material is then processed into product fractions or used as a more transportable material for further upgrading operations. Any unconverted 700° F.+ material is recycled and mixed with fresh feed to the hydro-isomerization reactor. Alternately, the pour point and viscosity of the synthesized liquids withdrawn from the HCS reactor may be reduced via hydroisomerization, to make a syncrude or a more pumpable and transportable material. The hydroisomerized material is withdrawn from the hydroisomerization unit 18 via line 34. The hydro-isomerization also results in the production of a hydrogen-rich tail gas comprising 95 volume % $H_2$ and containing 1 mole of the $H_2$ which is removed from the unit via line 36, and then passed via lines 36, 38 and 31 into HCS catalyst rejuvenation means (not shown) for rejuvenating the HCS catalyst which becomes reversibly deactivated due to the presence of reversible catalyst deactivating species present in the HCS reactor as outlined above. The HCS catalyst may be rejuvenated continuously or intermittently, either in-situ in the reactor or ex-situ in an external vessel as is known. Alternately, all or a portion of the $H_2$ may be passed, via lines 36 and 40 into the HCS reactor 14 as part of the synthesis feed. In a still further embodiment, all or a portion of the $H_2$ may be passed, via lines 36 and 28 into the hydrogen production unit 16, to provide more $H_2$ removed from the unit via line 30 for the hydroisomerization, etc. FIG. 2 illustrates the hydroisomerization unit 18 in greater detail. Referring to FIG. 2, hydroisomeri-zation unit 18 comprises fractionators 42 and 44 and hydroisomerization reactor 46. The liquid hydrocarbon products withdrawn from the HCS reactor are combined with hydrocarbon liquids condensed from the HCS reactor overheads (roughly $C_{11+}$) and passed, via line 32, into fractionator 42 which fractionates the feed into heavy and light fractions, with the heavier fraction removed via line 48, and the lighter fraction withdrawn via line 50. The heavier fraction, which includes 700° F.+ material, is passed via line 48 into a hydroisomerization reactor 46 in which it contacts and reacts with the hydrogen produced from the syngas passed into the reactor via line 30, in the presence of a suitable hydroisomerization catalyst as set forth above. The hydroisomerized hydrocarbons, which include a 700° F.+ fraction, along with gas comprising mostly unreacted hydrogen and water, are withdrawn from reactor 46 via line 52 and passed, after cooling by means not shown, into gas and liquid separator or knock-out drum 54, in which the hydrocarbon liquids and the water are separated from each other and from the unreacted hydrogen and minor amounts of unreacted methane, $C_{2+}$ hydrocarbon gasses and nitrogen. The water is removed via line 56 and the hydrogen-rich tail gas removed via line 36. The hydroisomerized hydrocarbons are removed via line 58 and passed into fractionator 44. Fractionator 44 produces a naphtha and a diesel fraction which are respectively removed via lines 60 and 62, with the remaining 700° F.+ material removed as bottoms via line 64 and recycled back into the hydroisomerization reactor 46, along with fresh feed from fractionator 42. In addition, minor amounts of light hydrocarbon gas are removed as overheads via line 63 and typically burned as fuel or passed to further processing. The unit is designed to accomplish 100% extinction of hydrocarbons boiling higher than 700° F. Typical hydroisomerization reactor conditions include an LHSV of about 1.3, 800–900 psia and a temperature of about 700–750° F. In this particular illustration, the ratio of recycle to fresh feed on a volumetric basis is about 0.5. Under these conditions, of the 5 moles of hydrogen fed into hydroisomerization reactor, 4 moles react with the hydrocarbons in the reactor. The unreacted 1 mole of hydrogen is removed from the reactor as tail gas via line 36.

Figure 3:
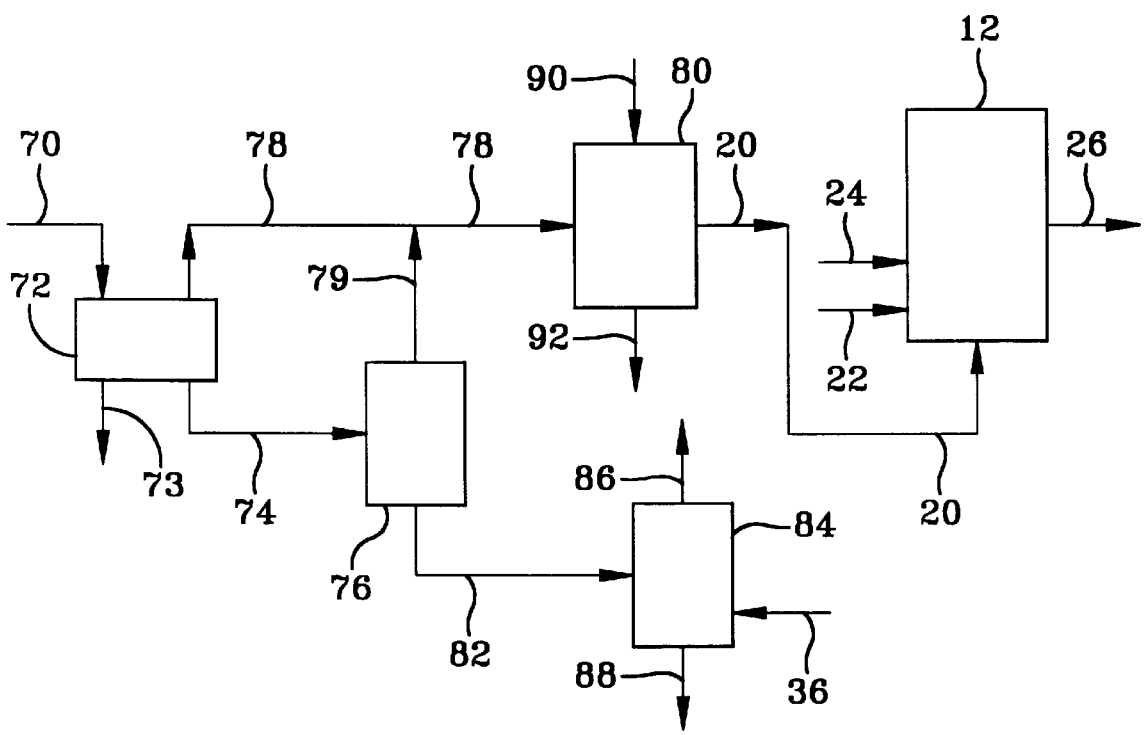
FIG. 3 shows an embodiment wherein natural gas well condensate liquids are recovered and hydrodesulfurized using the hydrogen-rich, hydroconversion reactor tail gas.

FIG. 3 illustrates an embodiment in which a portion of the hydrogen-rich tail gas is used to hydrodesulfurize sulfur-containing hydrocarbon liquids recovered from natural gas as condensate, with the natural gas further processed to remove sulfur and then used as feed for the syngas generator. Thus, a mixture of natural gas and sulfur-containing hydrocarbon liquids removed from a gas well (not shown) is passed, via line 70 into a gas-liquid separation vessel 72. The separated gas is passed to line 78. The separated hydrocarbon liquids are passed, via line 74, into a fractionator 76 which is at a lower pressure (e.g., a pressure of from about 50–300 psig) than that in 72. This removes more gas from the liquid condensate. This gas is passed into line 78 via line 79, where it is combined with the gas removed from the separation vessel. The gas-reduced condensate is then removed from the fractionator and passed into hydrodesulfurizer 84 via line 82. The hydrodesulfurizing is accomplished by contacting the hydrocarbon liquids with hydrogen in the presence of a suitable hydrodesulfurization catalyst, at conditions effective to remove most of the sulfur and nitrogen. Hydrodesulfurizing hydrocarbons for sulfur removal is well known and any conventional hydrodesulfurizing catalyst can be used, such as, Cyanamid's HDN-30; Katalco's NM-506; Ketjen's KF-840, etc. Such catalysts typically comprise Group VIII non-noble metals such as Ni and Co, and also Group VI metals such as Mo and W, supported on a refractory metal oxide support. The Groups referred to are the Groups in the Periodic Table of the Elements copyrighted by Sargent-Welch Scientific Company in 1968. A typical hydrodesulfurization catalyst comprises a mixture of nickel and molybdenum oxides supported on alumina. While hydrodesulfurizing conditions vary and may include a space velocity of from about 0.5–10 v/v/hr, from 200–350 psig hydrogen pressure and a gas treat rate of from about 300–1,000 SCF $H_2$/B, typical desulfurizing conditions in the practice of the invention include a space velocity of about 1 v/v/hr, 250 psig hydrogen and 600 SCF $H_2$/B. The hydrodesulfurizer contains a fixed bed of a hydrodesulfurizing catalyst comprising cobalt and molybdenum oxides on an alumina support as. The hydrogen rich tail gas is passed into the hydrodesulfurizer via line 36 and reacts with the condensate in the presence of the catalyst at conditions effective to remove the sulfur. The sulfur is removed as $H_2S$ via line 86 and sent to sulfur disposal. The hydrodesulfurized condensate hydrocarbon liquids are removed from the bottom of the hydrodesulfurizer via line 88. The condensate reduced natural gas is passed, via line 78, into a gas cleaning unit 80 in which sulfur compounds, and $CO_2$ if required, are removed to produce a sweet gas and in which additional hydrocarbon liquids may be recovered from the gas by condensation. The $CO_2$ and sulfur removal is accomplished by any well known means, such as scrubbing with an aqueous solution of a hindered amine and alcohol (e.g., 2-piperidine and ethanolsulfolane for removing the $H_2S$ and $CO_2$ from the gas, as is disclosed in U.S. Pat. No. 4,112,051) as is used in Exxon's Flexsorb PS® process. The amine solution enters the gas cleaning unit or scrubber 80 via line 90 and the sulfur laden solution is withdrawn via line 92. The sweet gas is then passed through other units and guard beds if necessary to further reduce the sulfur content and also remove nitrogen compounds, and then finally passed into the FBSG via line 20.

Figure 4:
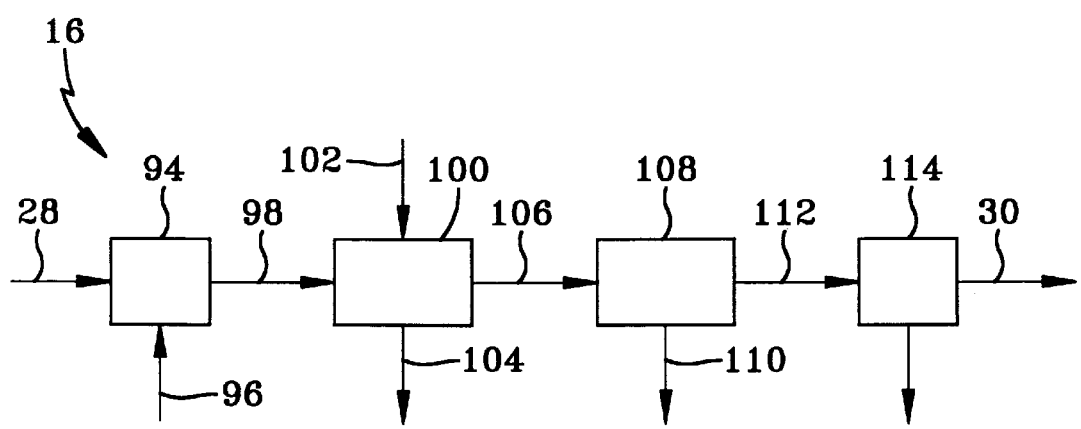
FIG. 4 is a block flow diagram of hydrogen production using a water gas shift reaction and PSA.

FIG. 4 illustrates another embodiment of the invention in which a water gas shift reactor is used to generate more hydrogen from the syngas slip stream, with the shift reactor effluent then passed through physical separation means to separate and recover the hydrogen. Turning to FIG. 4, a hydrogen producing means 16 comprises a water gas shift reactor 94, into which is fed the syngas slip stream via line 28, and steam via line 96 if the syngas doesn't contain enough water vapor. The shift reactor contains a water gas shift catalyst such as chromium oxide promoted iron oxide. In the shift reactor, the steam reacts with the CO in the presence of the catalyst to form one mole of $H_2$ and one mole of $CO_2$ for each mole of CO and $H_2O$ reacted, to produce a hydrogen rich gas. This gas which also contains $H_2O$ and any unreacted CO, exits the reactor and, after cooling and drum separation for water removal (not shown) is passed, via line 98, into scrubber 100 for $CO_2$ removal. Scrubber 100 is a conventional contacting tower containing inert packing or fractionation trays. A solvent, such as an aqueous amine solution or an aqueous hindered amine solution such as Flexsorb PS® containing 2-piperidine and ethanolsulfolane for removing the $CO_2$ from the gas, as is disclosed in U.S. Pat. No. 4,112,051, enters via line 102 and removes the $CO_2$. The particular solvent $CO_2$ removal system or other $CO_2$ removal means depends on the extent of $CO_2$ removal desired. If the Flexsorb PS® system is used, virtually all of the $CO_2$ is removed from the gas. The $CO_2$ laden solution is removed via line 104 and sent to solvent recovery, while the scrubbed vapor reduced in $CO_2$ is passed into heat exchanger and separation unit 108, via line 106, in which it is cooled to below 200° F. and the water removed via line 110. The cool gas which still contains water vapor, but not liquid water, is passed into PSA unit 114 via line 112. The PSA unit separates the hydrogen from the rest of the gas to produce 99% or higher purity hydrogen, which is removed via line 30 and used according to any or all of the embodiments above. The offgas resulting from the hydrogen separation is removed via line 34 and is typically used as a low BTU value fuel.

While the invention has been described in particular detail for an FBSG syngas generator using processed natural gas as the hydrocarbon feed to the generator, a slurry HCS unit and a hydroisomerization unit for the hydroconversion, the practice of the invention is not limited to these specific embodiments as those skilled in the art will know and appreciate. Thus, any suitable and convenient source of syngas, feed for the syngas generator and syngas generating process may be used, as may either fluid catalyst bed or fixed catalyst bed, non-slurry HCS processes. Similarly, the hydroconversion processes or processes will comprise at least one of those listed above.

It is understood that various other embodiments and modifications in the practice of the invention will be apparent to, and can be readily made by, those skilled in the art without departing from the scope and spirit of the invention described above. Accordingly, it is not intended that the scope of the claims appended hereto be limited to the exact description set forth above, but rather that the claims be construed as encompassing all of the features of patentable novelty which reside in the present invention, including all the features and embodiments which would be treated as equivalents thereof by those skilled in the art to which the invention pertains.

What is claimed is:

1. A gas conversion process comprising:
   (a) synthesizing hydrocarbons by reacting a synthesis gas comprising a mixture of $H_2$ and CO in the presence of a Fischer-Tropsch hydrocarbon synthesis catalyst, at reaction conditions effective to react said $H_2$ and CO to form hydrocarbons,
   (b) upgrading at least a portion of said synthesized hydrocarbons by reacting them with hydrogen, or a hydrogen containing gas, in the presence of a hydroconversion catalyst, to produce upgraded hydrocarbons and a hydrogen rich tail gas, and (c) using said hydrogen rich tail gas for at least one of (i) said hydrocarbon synthesis, (ii) hydrogen production, (iii) rejuvenation of said hydrocarbon synthesis catalyst, and (iv) hydrodesulfurization of sulfur-containing hydrocarbons.

2. A process according to claim 1 wherein said hydrocarbons are synthesized by reacting said $H_2$ and CO mixture in the presence of a Fischer-Tropsch hydrocarbon synthesis catalyst at reaction conditions effective to form hydrocarbons, at least a portion of which are solid at standard room temperature conditions of temperature and pressure.

3. A process according to claim 2 wherein said hydrocarbon synthesis catalyst comprises a catalytic cobalt component.

4. A process according to claim 3 wherein said hydrocarbon synthesis reaction occurs in a slurry comprising said hydrocarbon synthesis catalyst and bubbles of said $H_2$ and CO in a slurry liquid which comprises said synthesized hydrocarbons which are liquid at said reaction conditions.

5. A process according to claim 2 wherein said hydrocarbon synthesis becomes reversibly deactivated during said synthesis reaction and wherein said hydrogen-rich tail gas is used to rejuvenate said catalyst.

6. A process according to claim 2 wherein said synthesis gas is produced from natural gas from which sulfur-containing hydrocarbon liquids have been recovered and wherein said liquids are hydrodesulfurized by reacting with the hydrogen in said tail gas in the presence of a hydrodesulfurization catalyst.

7. A process according to claim 4 wherein said synthesis gas is produced from natural gas from which sulfur-containing hydrocarbon liquids have been recovered and wherein said liquids are hydrodesulfurized by reacting with hydrogen in said tail gas in the presence of a hydrodesulfurization catalyst.

8. A process according to claim 7 wherein said hydrocarbon synthesis becomes reversibly deactivated during said synthesis reaction and wherein said hydrogen-rich tail gas is used to rejuvenate said catalyst.

9. A gas conversion process comprising the steps of:

(i) removing a mixture of sulfur-containing natural gas and sulfur-containing hydrocarbon liquids from a gas well;

(ii) separating said natural gas from said sulfur-containing hydrocarbons;

(iii) removing sulfur from said natural gas to produce a sulfur-reduced natural gas;

(iv) passing said sulfur-reduced natural gas, oxygen and steam into a synthesis gas generator to produce a synthesis gas comprising a mixture of $H_2$ and CO;

(v) synthesizing hydrocarbons by reacting said $H_2$ and CO in said synthesis gas in the presence of a Fischer-Tropsch hydrocarbon synthesis catalyst, at reaction conditions effective to synthesize said hydrocarbons, wherein at least a portion of said synthesized hydrocarbons are solid at standard conditions of room temperature and pressure;

(vi) upgrading at least a portion of said synthesized hydrocarbons by reacting them with hydrogen, or a hydrogen containing gas, in the presence of a hydroconversion catalyst, to alter their molecular structure to produce upgraded hydrocarbons and a hydrogen rich tail gas, and (vii) using said hydrogen rich tail gas for at least one of (a) said hydrocarbon synthesis, (b) said hydrogen production, (c) rejuvenation of said hydrocarbon synthesis catalyst, and (d) hydrodesulfurization of said sulfur-containing hydrocarbons recovered from said natural gas well.

10. A process according to claim 9 wherein said hydrocarbon synthesis takes place in a three phase slurry in a slurry hydrocarbon synthesis reactor, wherein said slurry comprises gas bubbles and a solid particulate catalyst comprising a cobalt catalytic component, in a hydrocarbon slurry liquid, and wherein at least a portion of said synthesized hydrocarbons are liquid at the synthesis reaction conditions and comprise said slurry liquid.

11. A process according to claim 10 wherein a portion of said tail gas is used for said hydrocarbon synthesis.

12. A process according to claim 10 wherein a portion of said tail gas is used for said hydrogen production.

13. A process according to claim 10 wherein said hydrocarbon synthesis catalyst reversibly deactivates during said synthesis reaction and wherein said tail gas is used for rejuvenation of said catalyst.

* * * * *